US005871532A

United States Patent [19]
Schroeppel

[11] Patent Number: 5,871,532
[45] Date of Patent: Feb. 16, 1999

[54] EPICARDIAL LEAD FOR MINIMALLY INVASIVE IMPLANTATION

[75] Inventor: Edward A. Schroeppel, Lake Jackson, Tex.

[73] Assignee: Sulzer Intermedics Inc., Angleton, Tex.

[21] Appl. No.: 861,643

[22] Filed: May 22, 1997

[51] Int. Cl.⁶ ................................................. A61N 1/00
[52] U.S. Cl. ............................................................ 607/128
[58] Field of Search .................................. 607/119, 122, 607/126, 127, 128, 130

[56] References Cited

U.S. PATENT DOCUMENTS

| | | |
|---|---|---|
| 3,902,501 | 9/1975 | Citron et al. . |
| 3,939,843 | 2/1976 | Smyth . |
| 3,943,936 | 3/1976 | Rasor et al. . |
| 4,233,992 | 11/1980 | Bisping . |
| 4,378,023 | 3/1983 | Trabucco . |
| 4,567,901 | 2/1986 | Harris . |
| 4,585,013 | 4/1986 | Harris ...................................... 607/126 |
| 4,721,118 | 1/1988 | Harris . |
| 4,858,623 | 8/1989 | Bradshaw et al. . |
| 5,115,818 | 5/1992 | Holleman et al. . |
| 5,179,962 | 1/1993 | Dutcher et al. . |
| 5,257,634 | 11/1993 | Kroll . |
| 5,314,462 | 5/1994 | Heil et al. ................................ 607/128 |
| 5,385,579 | 1/1995 | Helland ................................... 607/130 |
| 5,476,500 | 12/1995 | Fain et al. ................................ 607/126 |
| 5,571,162 | 11/1996 | Lin ........................................... 607/122 |
| 5,601,614 | 2/1997 | Ekwall ...................................... 607/25 |

FOREIGN PATENT DOCUMENTS 0 004 967A2  4/1979  European Pat. Off. .
3529578 A1  2/1987  Germany .

OTHER PUBLICATIONS

Kevin Morgan et al., A New Single Pass DDD Lead, all pages, 8 May 1997.
Peter P. Karpawich, "Septal Pacing : A New Appraoch to Improve Paced Left Ventricular Function".
European Journal of Cardiac Pacing & Electrophysiology, vol. 6, No. 1, p. 143, Jun. 1996.
R. McVenes, "What Tools Do We need For Multi Site Stimulation?"; European Journal of Cardiac Pacing Electrophysiology, vol. 6, No. 1, p. 145, Jun. 1996.

Primary Examiner—Scott M. Getzow
Attorney, Agent, or Firm—John R. Merkling; Timothy M. Honeycutt

[57] ABSTRACT

A lead assembly for fixation to a human heart via thoracoscopy is provided. The lead assembly includes a lead that has a connector for connection to a cardiac stimulator, such as a pacemaker, a cardioverter/defibrillator, or a sensing instrument. A fixation mechanism is coupled to the lead that includes a tubular housing and a proximally projecting hook that is adapted to engage heart tissue. The hook is pivotable between a retracted position and an extended position. The lead and the hook are manipulated by a stylet. The lead assembly also includes a tubular introducer that is passed through the chest wall of a patient and used to place the lead proximate the epicardium.

22 Claims, 5 Drawing Sheets

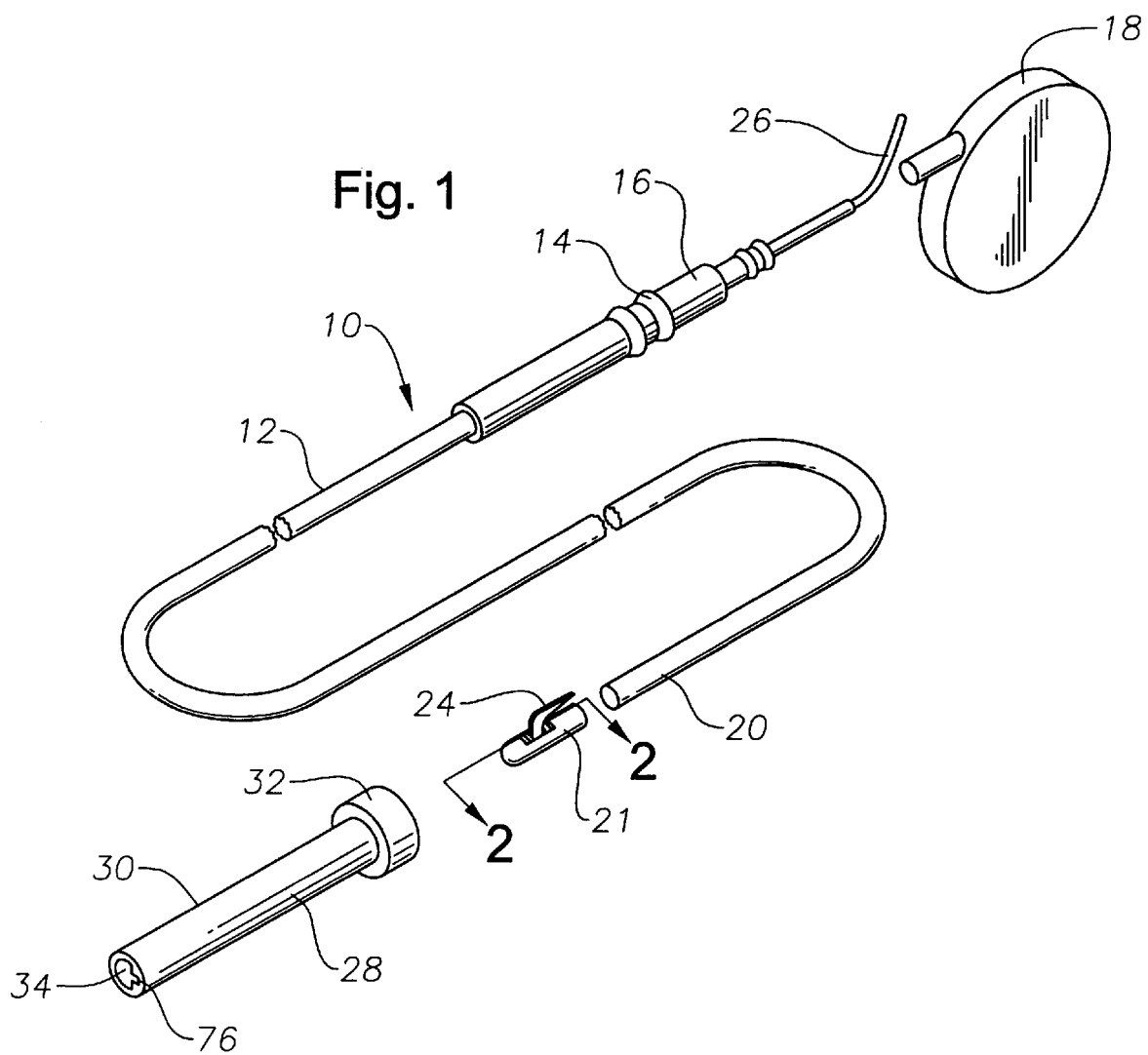
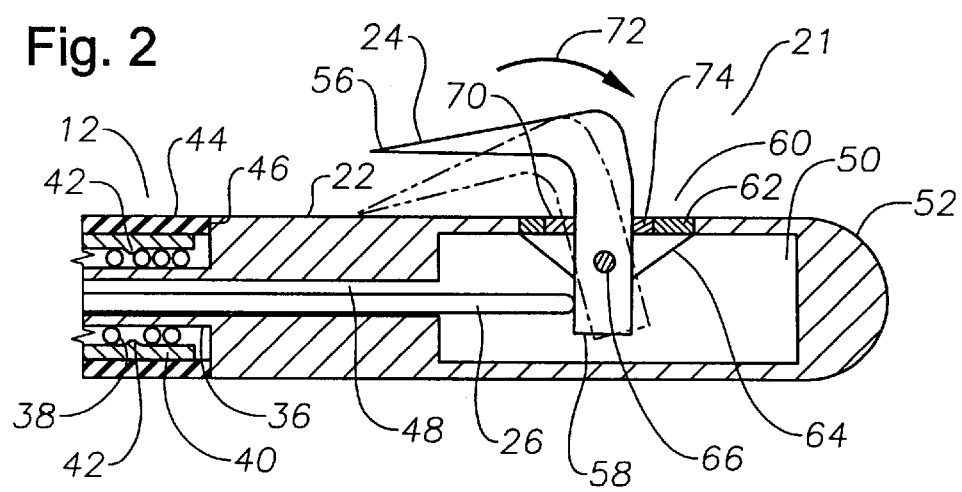

EPICARDIAL LEAD FOR MINIMALLY INVASIVE IMPLANTATION

BACKGROUND OF THE INVENTION

1. Field of the Invention

This invention relates generally to implantable cardiac stimulation leads. More particularly, this invention relates to actively fixated epicardial leads for cardiac stimulation.

2. Description of the Related Art

Prior to the advent of endocardially implanted leads and associated surgical implantation techniques, surgeons and cardiologists traditionally relied on epicardial leads for cardiac stimulation and diagnosis. Median sternotomy or anterior thoracotomy were commonly used techniques to access the pericardium for epicardial lead implantation. Both techniques involve a significant incision and the post-operative issues associated with large incisions, such as recuperation time, pain, risk of infection, and cosmetic results.

Patients and practitioners alike favor the use of endocardial leads for cardiac stimulation in most circumstances. The benefits of transvenous implantation are many, including improved post-operative cosmetic appearance, faster wound healing, less post-operative pain, and improved flexibility in electrode placement. In addition, many areas of the myocardium that do not normally lend themselves to epicardial stimulation, such as the interventricular septum or the coronary sinus, may be readily paced endocardially.

Despite the advantages associated with endocardial implantation, epicardial cardiac stimulation is still medically indicated for many patients, particularly children. Although the various indications for epicardial lead fixation in pediatric patients are numerous, some common factors include small stature, congenital heart defects with residual or potential right to left shunting, or lack of venous access to the chamber requiring pacing.

Early designs for epicardial leads required relatively large screw-in electrodes that were intended for ventricular applications only. Follow-on prior art electrode designs utilized a stab-on electrode that was configured to be inserted into the atrial or the ventricular myocardium in a direction almost tangential to, and just under, the epicardial surface. After the stab-on step, the electrode body was then sutured to the myocardium for stabilization. These prior art electrodes were most commonly implanted via median sternotomy or anterior thoracotomy The advent of thoracoscopy in cardiac surgery has shown promise as a technique to enable surgeons to implant epicardial leads without sternotomy or thoracotomy. Thoracoscopy normally involves penetration of the chest cavity with two or more tubular introducers that are passed through small incisions in the chest wall. Illumination devices, cutting instruments, sutures, etc. may be inserted into the chest cavity via the introducers.

Despite the promise of thoracoscopy, many conventional epicardial leads utilize a widened suture pad that is normally disk-shaped and includes one or more suture holes for guiding a suture needle into the epicardium. These disk-like suture pads may present the surgeon with certain difficulties during insertion via a typical thoracoscopy introducer. To begin with, there is the potential for the suture pad to resist movement through the introducer. Unless extreme caution is exercised, the lead may be damaged. To avoid the potential for snagging the lead, surgeons may have to use a larger than necessary introducer, resulting in a larger incision, more scarring, and potentially more post-operative pain for the patient. In addition, if a conventional suture pad epicardial lead must be relocated due to improper threshold or some other indication, the surgeon must expend time and effort cutting the existing sutures and sewing the pad to the new location.

Another solution proposed for epicardial lead implantation utilizes a sutureless screw-in electrode. The electrode is screwed into the epicardium perpendicular to the surface of the epicardium while the lead is laid approximately parallel to the epicardium surface. The arrangement produces an almost 90° bend in the lead just proximal to the electrode that may give rise to forces capable of dislodging the electrode and/or injuring the epicardium, particularly in view of the normally vigorous cyclic movement of the epicardium. Injury to the epicardium may also occur if the rib cage is compressed against the 90° bend during rough play or other exercise.

Another existing lead design incorporates a projectable side hook that is normally biased in a retracted position by a coil spring. The side hook is moved to an extended position by application of axial force from a stylet to an internally disposed leg of the side hook that includes a roller disposed in an arcuate channel. The fabrication of this system requires a series of complex molding and machining steps, often under relatively tight tolerances. In operation, this system relies on a series of cooperating rollers, curved slots, and springs that may be subject to malfunction during implantation, and requires the surgeon to simultaneously apply axial force on a stylet and torsional force on the lead.

The present invention is directed to overcoming or reducing one or more of the foregoing disadvantages.

SUMMARY OF THE INVENTION

In accordance with one aspect of the present invention, an active fixation mechanism for securing a cardiac lead to heart tissue is provided. The active fixation mechanism includes a tubular housing that is coupled to the lead and has a lumen. A hook is provided that has a first end that is pivotally coupled to the housing. A portion of the first end of the hook is disposed in the lumen. The hook also has a first longitudinally projecting piercing member. The hook is pivotable between a first position wherein the first piercing member is disposed in spaced apart relation to the housing, and a second position wherein the first piercing member is disposed proximate to the housing. A biasing member is coupled to the housing to bias the hook to the first position. The hook pivots to the second position in response to application of axial force to the portion of the first end to avoid piercing engagement with the heart tissue, and pivots to the first position when force is removed so that the first piercing member of the hook may engage the heart tissue.

In accordance with another aspect of the present invention, a lead for fixation to heart tissue is provided. The lead includes an elongated elastic insulating tubular sheath and a tubular housing that is coupled to the sheath and has a lumen. A hook is provided that has a first end pivotally coupled to the housing and a first longitudinally projecting piercing member. A portion of the first end is disposed in the lumen. The hook is pivotable between a first position wherein the first piercing member is disposed in spaced apart relation to the housing, and a second position wherein the first piercing member is disposed proximate to the housing. A biasing member is coupled to the housing to bias the hook to the first position. The hook pivots to the second position in response to application of axial force to the portion of the first end to avoid piercing engagement with the heart tissue, and pivots to the first position when force is removed so that the first piercing member of the hook may engage the heart tissue.

In accordance with still another aspect of the present invention, a lead assembly for fixation to heart tissue is provided. The lead assembly includes an elongated tubular lead that has a first distal end. A tubular housing is coupled to the distal end and has a lumen. A hook is provided that has a first end coupled to the housing and first longitudinally projecting piercing member that is disposed in a spaced apart relation to said housing. A tubular introducer is provided that has a lumen for slidably receiving the lead. The introducer has a second distal end, an interior surface, and a guide slot in the interior surface to slidably receive the hook. The housing may be projected from the distal end in a preselected angular orientation.

In accordance with yet another aspect of the present invention, an active fixation mechanism for securing a cardiac lead to heart tissue is provided. The active fixation mechanism includes a tubular housing coupled to the lead. A screw-in hook is provided that has a first end pivotally coupled to the housing and a second end for piercing the heart tissue. The lead may be pivoted to lay generally parallel to said heart tissue after the screw-in hook is screwed into the tissue.

In accordance with yet another aspect of the present invention, a lead assembly for fixation to heart tissue is provided. The lead assembly includes an elongated tubular lead. A tubular hook assembly is disposed around and coupled to the housing. The hook assembly has a proximally projecting hook for engaging the heart tissue.

BRIEF DESCRIPTION OF THE DRAWINGS

The foregoing and other advantages of the invention will become apparent upon reading the following detailed description and upon reference to the drawings in which:

FIG. 1 is a pictorial view of an epicardial lead assembly in accordance with the present invention;

FIG. 2 is a sectional view of FIG. 1 taken at section 2—2 showing a detail of the fixation mechanism for the lead assembly in accordance with the present invention;

DETAILED DESCRIPTION OF SPECIFIC EMBODIMENTS

Figure 3:
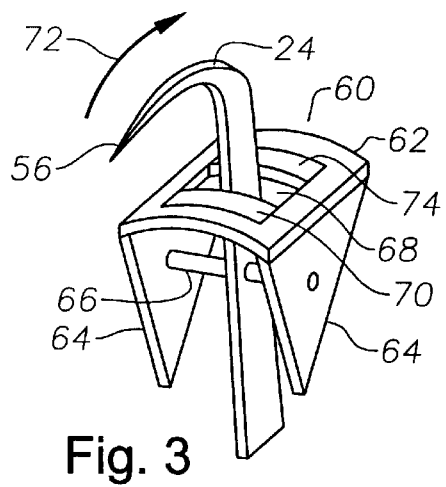
FIG. 3 is a pictorial view of the support assembly for the hook of the fixation mechanism in accordance with the present invention.
Figure 5:
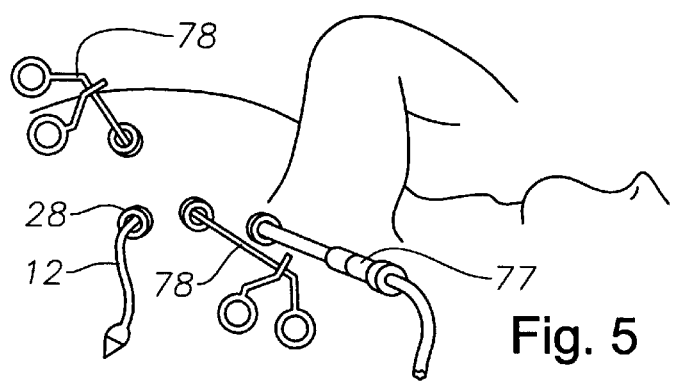
FIG. 5 is a side view of a patient showing the arrangement of various thoracoscopy instruments used during implantation.

Turning now to the drawings, and in particular to FIGS. 1 and 2, there is shown an exemplary lead assembly 10 that is adapted for either epicardial or endocardial fixation to a human heart. Note that reference numerals are generally reused in the figures where identical elements appear in more than one figure.

The lead assembly 10 includes a lead 12 that has a proximal end 14 provided with a connector 16 for electrical connection to a cardiac stimulator 18. The cardiac stimulator 18 may be a pacemaker, a cardioverter/defibrillator, or a sensing instrument. At the distal end 20 of the lead 12, a fixation mechanism 21 is coupled that includes a tubular housing 22 and a proximally projecting hook 24 that is adapted to engage heart tissue as set forth below. The lead 12 is manipulated by a stylet 26 that is inserted into the lead 12. The lead assembly 10 also includes a tubular introducer 28 that has an elongated distal portion 30 and a proximal portion 32 with a diameter larger than the distal portion 30 to act as a shoulder to prevent the introducer 28 from sliding entirely inside the chest cavity. A lumen 34 extends through the introducer 28 to slidably receive the lead 12. As discussed more below, the introducer 28 is passed through the chest wall of a patient and used to place the lead 12 proximate the epicardium.

The detailed structure of the lead 12, the fixation mechanism 21, and the housing 22 may be understood by reference to FIG. 2, which is a sectional view of FIG. 1 taken at section 2—2. The housing 22 has a proximally projecting reduced diameter portion 36 around which is wound the distal end of a conducting coil 38 that is connected proximally with the connector 16. The conductor coil 38 is snugly pressed against the portion 36 by a tubular crimp sleeve 40 that is slipped over the distal end of the conductor coil 38 and crimped tightly at the locations 42 as indicated. In this way, an electrical pathway is established between the connector 16 and the housing 22. The conductor coil 38, the crimp sleeve 40, and the reduced diameter portion 36 are covered with a tubular insulating sleeve 44, composed of a conventional biocompatible material such as polyurethane or silicone, which abuts against the annular shoulder 46 of the housing 22.

The lead 12 has a lumen 48 that is coterminous proximally with the connector 16 and extends to the distal end of the housing 22. The lumen 48 terminates distally in a larger diameter cylindrical chamber 50. The housing 22 terminates distally in a rounded tip 52. The crimping sleeve 40 may be composed of a biocompatible ductile material, such as, for example, 316 stainless steel. The conductor coil 38 may be any of a variety of different types of conductor coils utilized in cardiac leads, such as, for example trifilar, bipolar coaxial, or Thinline™ (trademark of Sulzer Intermedics, Inc.). The sleeve 44 is secured to the annular shoulder 46 by any suitable biocompatible medical grade adhesive, such as Dow Medical Adhesive Silicone Type A, to retard the entry of body fluids into the lead at the annular shoulder 46. In the embodiment shown in FIG. 2, the housing 22 is electrically connected to the conductor coil 38 and functions as an electrode for carrying electrical signals to or from the heart muscle. Accordingly, the housing 22 may be fabricated from a variety of biocompatible conducting materials, such as titanium, platinum iridium alloy, iridium oxide coated platinum, stainless steel, or similar materials.

The hook 24 has a proximally projecting highly tapered end 56 that is designed to pierce heart tissue. The end 56 is generally longitudinally aligned with the longitudinal axis of the housing 22. The other end or base 58 of the hook 24 is pivotally coupled to the housing 22 by means of a pivot assembly 60.

The hook 24 may be fabricated from a variety of biocompatible materials, such as, for example, stainless steel, titanium, platinum, iridium oxide coated platinum, or similar materials.

The structure and operation of the support assembly 60 may be understood by reference, additionally, to FIG. 3, which shows a pictorial view of the support assembly 60 removed from the housing 22. The support assembly 60 includes a top plate 62 that has a radius of curvature corresponding to the radius of curvature of the housing 22. Two downwardly projecting gussets 64 are coupled to the underside of the top plate 62 in spaced apart and parallel relation. The hook 24 is pivotally coupled to the gussets 64 by a pivot pin 66. The upper portion of the hook 24 projects through an opening 68 in the top plate 62. At the proximal side of the opening 68 a biasing member 70 is coupled to the top plate 62. The biasing member 70 is dimensioned to bear against the proximal side of the hook 24 and bias the hook 24 to the position shown in FIG. 2. The biasing member 70 is preferably composed of a biocompatible elastomeric material that is suitable for providing a biasing force, such as silicone rubber or other suitable biocompatible elastomeric material. Alternatively, the biasing member 70 may be a coil or other type of spring fabricated from a biocompatible material, such as stainless steel or titanium.

The hook 24 and the housing 22 are configured so that the hook 24 may pivot from the position shown in solid line FIG. 2 to the position shown in phantom in FIG. 2. However, in order to achieve a suitable engagement with heart tissue as well as minimize the possibility that the piercing end 56 of the hook 24 catches on the introducer 28 during implantation, it is desirable to prevent the hook 24 from rotating in the direction of the arrow 72 beyond the position shown in FIG. 2. Accordingly, the distal side of the opening 68 is provided with a relatively rigid member 74 that is coupled to the top plate 62 and bears against the distal side of the hook 24 to prevent rotation in the direction of the arrow 72 beyond the position shown in FIG. 2. The rigid member 74 may be semi-annular as shown in FIG. 3 or any of a number of other shapes that provide a stop surface against further rotation of the hook 24. The support assembly 60 may be prefabricated as a modular assembly as shown in FIG. 3 and snapped into position through an opening in the housing 22. Alternatively, the support assembly 60 may be divided into two halves, each of which includes a gusset 64, that are incorporated directly into the housing 22 and assembled along with the two halves of the housing 22 during final assembly. As noted above, the hook 24 is pivotal between the two positions shown in FIG. 2. The surgeon may selectively pivot the hook 24 by appropriate manipulation of the stylet 26. Axial force applied on the stylet 26 against the lower end 58 of the hook 24 causes the hook 24 to pivot from the position shown in solid line in FIG. 2 to the position shown in phantom in FIG. 2. Conversely, when the stylet 26 is retracted, the biasing member 70 causes the hook 24 to pivot back to the position shown in solid line in FIG. 2.

Figure 4:
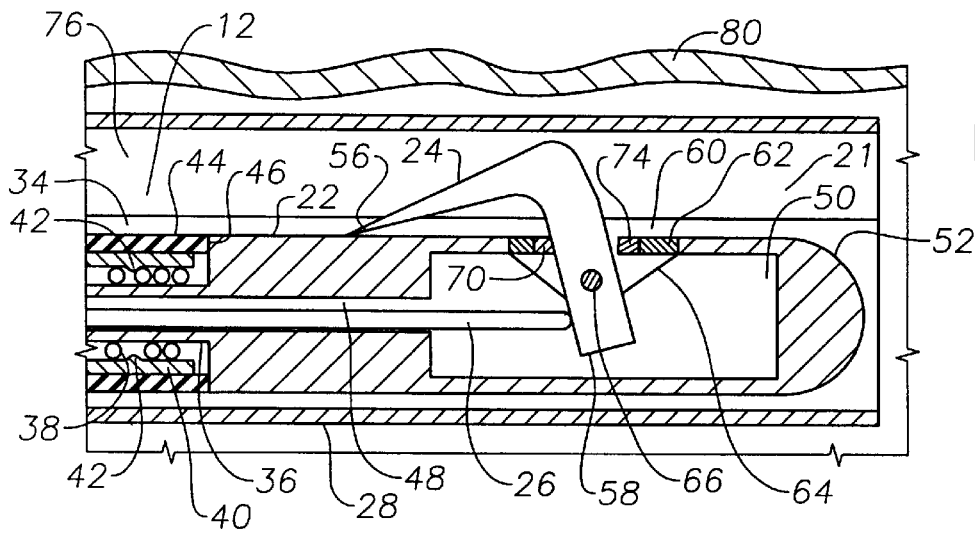
FIG. 4 is a partial sectional view of the fixation mechanism and the lead disposed in a tubular introducer during epicardial implantation in accordance with the present invention.

Referring now to FIGS. 1 and 4, the coterminous lumen 34 of the introducer 28 is advantageously dimensioned to have a slightly larger diameter than the lead 12. The introducer 28 is provided with a guide slot 76 to not only accommodate the radially projecting hook 24, but also to enable the surgeon to readily rotate the lead 12 by rotating the introducer 28. In this way, the lead 12 can be projected from the introducer 28 with the hook 24 in a known angular orientation relative to the epicardium, thus reducing the amount of manipulation via the grasping devices 77 necessary to place the lead 12. The geometry of the introducer 28 may vary from what is shown in FIG. 1. The introducer 28 may be fabricated from a variety of known materials, such as polyurethane or similar materials, or from a radiopaque material such as stainless steel.

Figure 6:
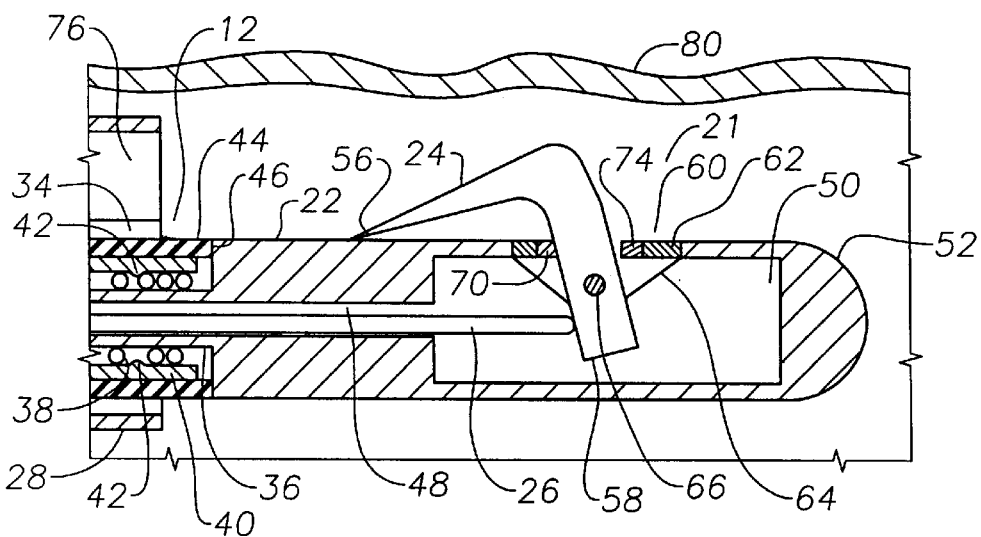
FIG. 6 is a partial sectional view of the lead and the fixation mechanism during implantation and after the fixation mechanism has been projected distally from the introducer in accordance with the present invention.
Figure 7:
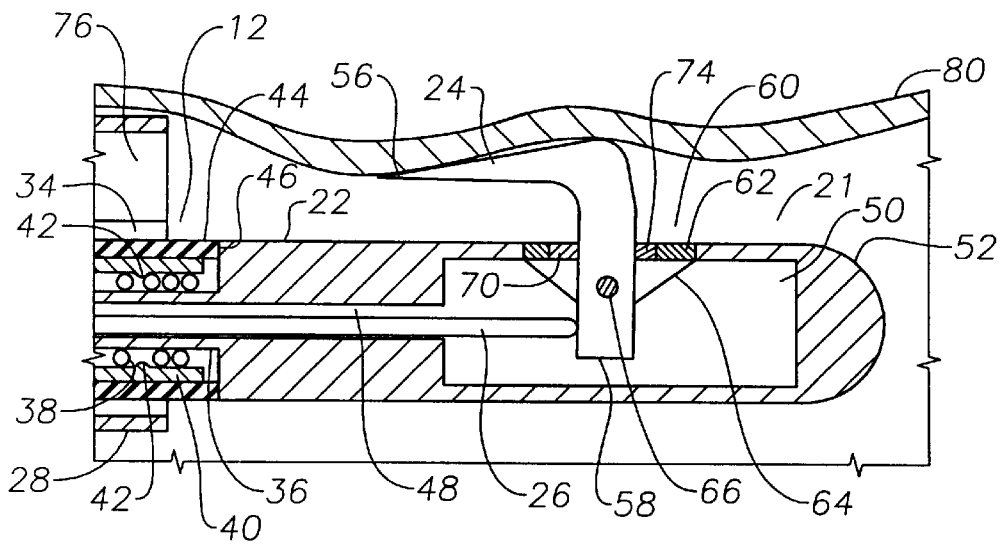
FIG. 7 is the same view as FIG. 6 with the engaging hook pivoted to an engagement position in accordance with the present invention.

The implantation and operation of the lead assembly 10 using thoracoscopy in an epicardial implantation context may be understood by reference to FIGS. 4, 5, 6, and 7. The description is intended to be illustrative, as the exact implantation procedure employed for a given patient, including the number, type, and placement of instruments may vary depending on the patient and the surgeon. The introducer 28 is passed into the chest via a small incision in one of the intercostal spaces and the lead 12 is passed into the introducer 28. A thoracoscope 77 is introduced into the chest in a similar manner. One or more grasping devices 78 may also be inserted, as necessary. Prior to inserting the lead 12 into the introducer 28, the stylet 26 is passed through the lumen 48 and thrust against the lower end 58 of the hook 24 to pivot the hook 24 to the position shown in FIG. 4. After the lead 12 is inserted into the introducer 28, the lead 12 is advanced to the distal end of the introducer 28 and the introducer 28 is positioned adjacent to the particular attachment location on the epicardium 80, shown in section. While maintaining axial force on the lower end 58 via the stylet 26, the lead 12 is advanced out of the distal end of the introducer 28 as shown in FIG. 6. After the housing 22 and the hook 24 have cleared the introducer 28, the stylet 26 is withdrawn a short distance to enable the biasing member 70 to pivot the hook 24 to the position shown in FIG. 7. At this point, application of tension to the proximal end 14 of the lead 12 will bring the hook 24 into piercing engagement with the epicardium 80.

During many implantation procedures, the initial placement of the lead 12 proves unsatisfactory for a variety of reasons, such as undesirable thresholds or an inadequate piercing engagement by the hook 24. If the lead 12 must be disengaged from the epicardium 80 and repositioned or removed completely, the foregoing implantation procedure is reversed. Referring again to FIG. 7, the stylet 26 is reintroduced into the lumen 48 and axial force is applied to the stylet 26 to push the lead 12 longitudinally and bring the hook 24 out of piercing engagement with the epicardium 80. Note that this particular step should be done without applying tension to the proximal end 14 of the lead 12 so that application of the axial force by the stylet 26 does not pivot the hook 24 while the lead 12 is being disengaged from the epicardium 80. Once the hook 24 has cleared the epicardium 80, tension is again applied to the proximal end of the lead 12 so that the stylet 26 pivots the hook 24 to the position shown in FIG. 6. At this point, the lead 12 is withdrawn into the introducer 28. The presence of the slot 76 will allow the housing 22 to reenter the introducer 28 only in the angular orientation where the hook 24 is aligned with the slot 76. If the slot and the hook 24 are not longitudinally aligned, either the introducer 28 or the lead 12 may be rotated until the necessary alignment is achieved. The foregoing implantation procedure may then be repeated to fix the lead to a new location. The skilled artisan will appreciate that the foregoing implantation and detachment procedures may be repeated as often as necessary to achieve the desired fixation.

Figure 8:
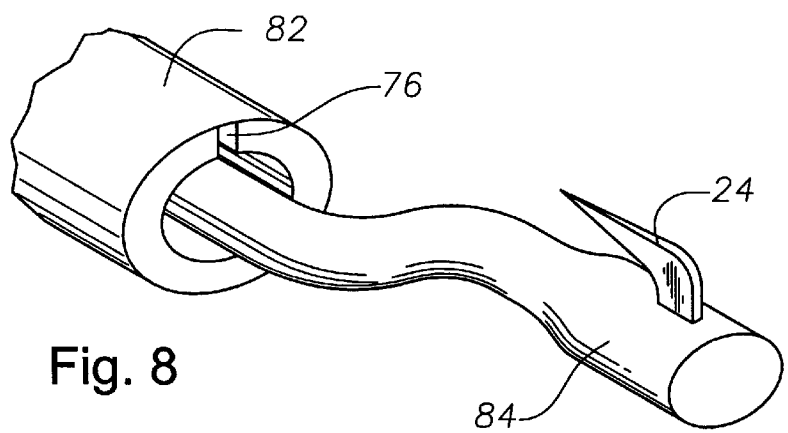
FIG. 8 is a pictorial view of the distal ends of an alternative embodiment of the introducer and the lead housing in accordance with the present invention.

FIG. 8 shows a pictorial view of an alternative configuration for an introducer 82 and a housing 84 that provides rapid retraction of the housing 84 in a known angular position into the introducer 82. The introducer 82 and the housing 84 are both provided with the same general cross-section, in this case an elliptical cross-section. The proximal end of the housing 84 is rounded and inwardly tapered so that, as the housing 84 is drawn into the introducer 82, the engagement of the surfaces of the introducer 82 and the housing 84 automatically bring the housing 84 into position so that the hook 24 is angularly aligned with the slot 76. Thus, the housing 84 and the introducer 82 are selfaligning so that the surgeon need not rotate either the introducer 82 or the housing 84 to achieve the necessary alignment for retraction.

Figure 9:
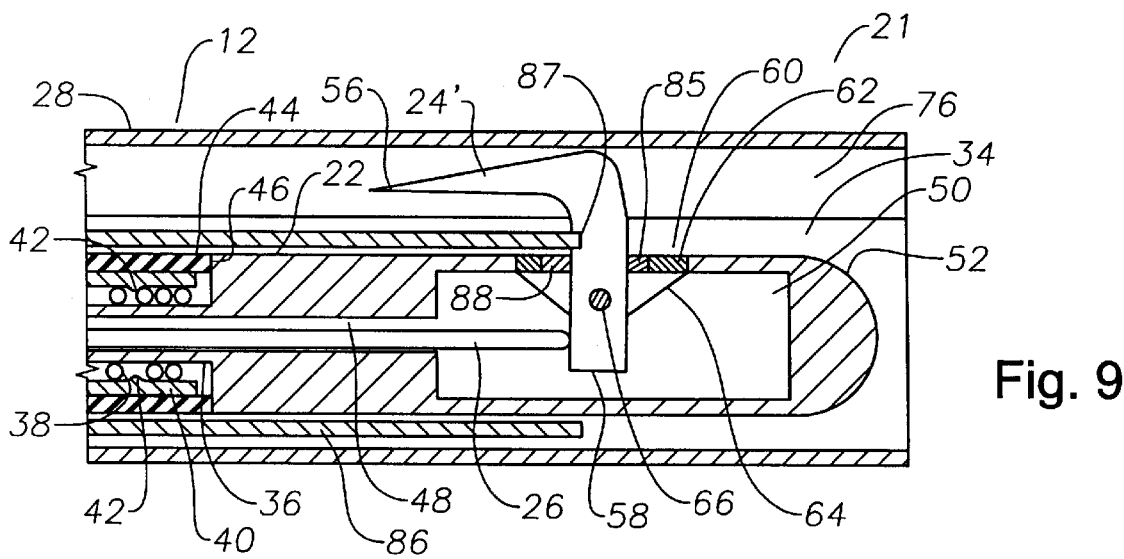
FIG. 9 is a partial sectional view of an alternative lead assembly incorporating a tubular sleeve for manipulating the hook in accordance with the present invention.

In an alternative arrangement shown in FIG. 9, pivotal manipulation of the hook 24' is accomplished by the interplay between a biasing member 85 that is coupled to the support assembly 60 distal to a modified hook 24' and a tubular sleeve insert 86 that is slipped over the lead 12 prior to inserting the lead into the introducer 28. In the absence of the insert sleeve 86, the hook 24' is biased by the biasing member 85 to the position shown in phantom. However, when the insert sleeve 86 is slipped over the lead 12 the distal end of the insert sleeve 86 engages a slot 87 on the proximal side of the hook 24'. Axial force from the insert sleeve 86 applied against the hook 24' in combination with tension applied at the proximal end of the lead 12 urges the hook 24' to pivot to the position shown in solid line in FIG. 8. A barrier pad 88 is coupled to the support assembly 60 proximal to the hook 24' to provide a pliable surface against which the hook 24' may engage when the insert sleeve 86 is removed. The barrier 88 should have a higher elasticity than the biasing member 85 so that the biasing member 85 can readily pivot the hook to the position shown in phantom. During implantation, the insert sleeve 86 is slipped over the lead 12 and the combined lead and insert sleeve 86 are inserted through the introducer 28 into the chest cavity positioned as discussed above. The insert sleeve 86 is then projected distally from the introducer to position the hook 24' proximate the desired fixation position near the epicardium. When the desired location is reached, tension is applied to the proximal end 14 of the lead 12 and the insert sleeve 86 is withdrawn slightly so that the hook 24' may make piercing engagement with the epicardium. The insert sleeve 86 is then withdrawn. When the insert sleeve 86 loses engagement with the slot 87, the biasing member 85 pivots the hook 24' to the position indicated in phantom, thereby providing a forcep-like engagement with the epicardium. The stylet 26 is not necessary to manipulate the hook 24', but may be employed to aid in positioning the lead 12.

Figure 10:
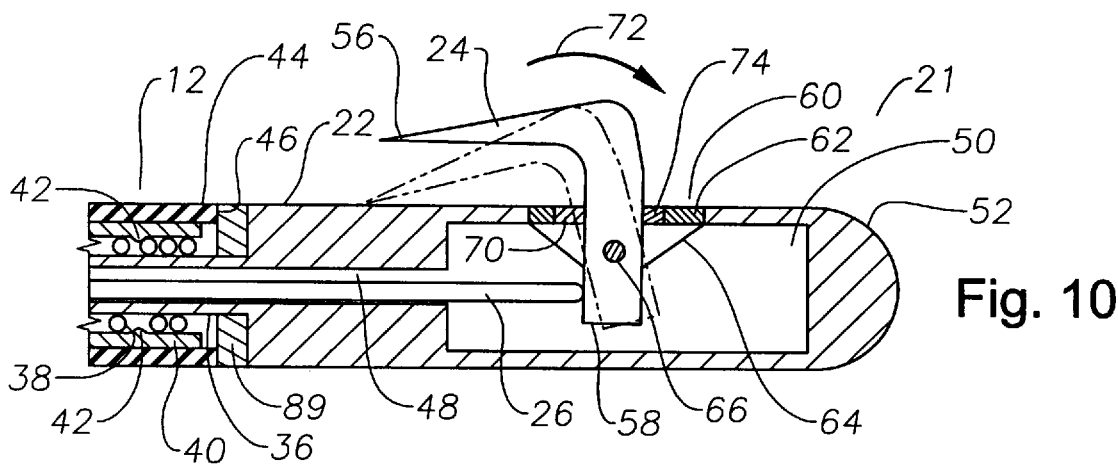
FIG. 10 is a partial sectional view of the fixation mechanism and lead showing an annular electrode coupled to the fixation mechanism proximal to the hook in accordance with the present invention.

The skilled artisan will appreciate that the lead assembly, and particularly the housing 22 and the hook 24 may take on a variety of different configurations. For example, as shown in FIG. 10, the housing 22 may be fitted with an annular electrode 89 that is in physical engagement with the conducting coil 38 to provide an electrical pathway to the epicardium. Because the annular electrode 89 is providing the electrical pathway, the housing 22 need not be constructed of a conducting material. In such circumstances, the housing 22 may be fabricated from any conventional biocompatible electrically insulating material suitable for use in leads, such as polyurethane or Delrin.

Figure 11:
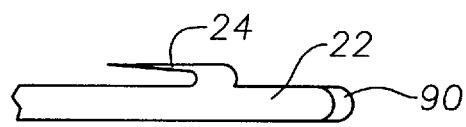
FIG. 11 is a side view of an alternative fixation mechanism wherein an electrode is coupled to the fixation mechanism distal to the hook in accordance with the present invention.
Figure 12:
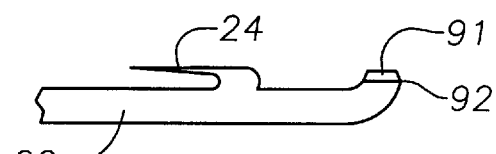
FIG. 12 is a side view of another alternative of the fixation mechanism wherein an electrode is coupled to the fixation mechanism in longitudinal alignment with the hook in accordance with the present invention.
Figure 13:
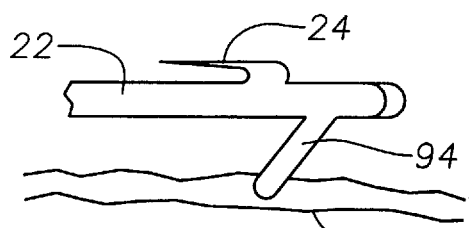
FIG. 13 is another alternative arrangement for the fixation mechanism wherein a tine is provided to enable passive fixation with a pericardial sac in accordance with the present invention.
Figure 14:
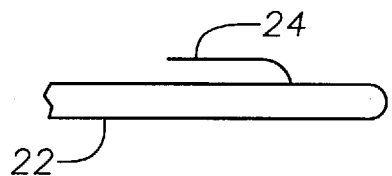
FIG. 14 is a side view of an alternative arrangement of the fixation mechanism wherein the hook is formed from a thin proximally projecting wire in accordance with the present invention.
Figure 15:
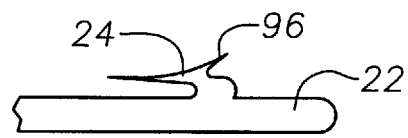
FIG. 15 is a side view of another alternative of the fixation mechanism wherein the hook is provided with a distally projecting barb to provide further engagement with the epicardium in accordance with the present invention.

Several other alternative configurations for the fixation mechanism are provided in FIGS. 11,12,13,14, and 15. As shown in FIG. 11, the housing may be provided with an electrode 90 that is located distally from the hook 24. As shown in FIG. 12, the housing 22 may be fitted with an electrode 91 that is both located distally from the hook 24 and is also positioned on a radially projecting prominence 92 formed in the housing 22. The prominence 92 is longitudinally aligned with the hook 24 so that when the hook 24 is brought into piercing engagement with the epicardium the electrode 91 will be located very close to the epicardium. As shown in FIG. 13, the housing 22 may be provided with a tine 94 to provide a passive engagement with the pericardial sac 95 in addition to the active fixation of the hook 24 to the heart tissue. As shown in FIGS. 14 and 15, the hook 24 may take on a variety of geometries. The hook 24 in FIG. 14 consists of a proximally projecting thin wire that is coupled to a widened base disposed in the housing 22 that is engageable with a stylet (not shown). In another alternative shown in FIG. 15, the hook 24 is provided with a distally projecting end or barb 96 that engages the epicardium to restrict longitudinal movement of the housing 22 distally after the hook 24 has been brought into piercing engagement with the epicardium.

Figure 16:
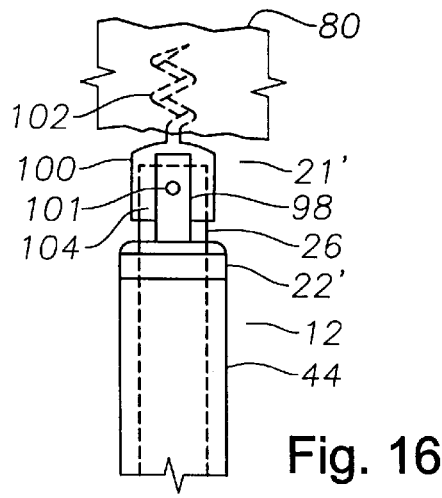
FIG. 16 is a side view of an alternative fixation mechanism that includes a screw-in hook pivotally coupled to a lead.
Figure 17:
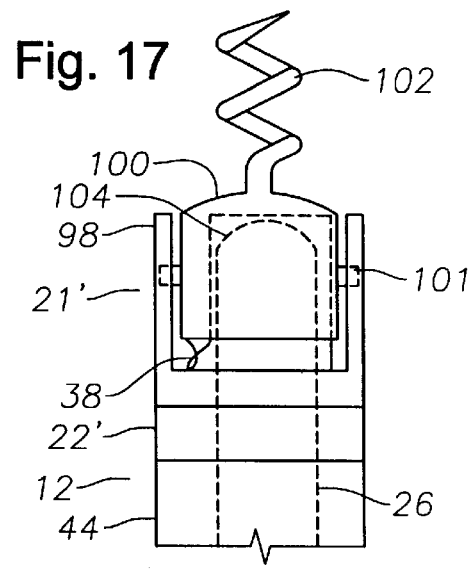
FIG. 17 is a front view of FIG. 16.

In alternate embodiments shown in FIGS. 16, 17, 18, and 19, a fixation mechanism 21' utilizing a screw-in lead tip may be employed that obviates the troublesome 90° bends associated with conventional screw-in epicardial leads. FIGS. 16 and 17 show, respectively, front and side views of the fixation mechanism 21' attached to the lead 12 described above. The fixation mechanism 21' includes a tubular housing 22' secured to the sleeve 44 as described above. The distal end of the housing includes a support fork 98 that pivotally supports a hook support 100 via a pivot pin 101. A screw-in hook 102 is coupled to, and projects distally from, the hook support 100. The proximal end of the hook support 100 includes a bore 104 (shown in phantom) for receipt of the stylet 26 (shown partially in phantom). The hook 102 may serve as an electrode by coupling the conductor coil 38 disclosed above to the proximal end of the hook support 100 offset from the bore 104 to avoid the stylet 26. The conductor coil 38 should be sufficiently flexible to withstand the bending associated with the pivoting of the hook support 100. The various components of the fixation mechanism 21' may be fabricated from the same types of materials proposed for the housing 22 discussed above.

Figure 18:
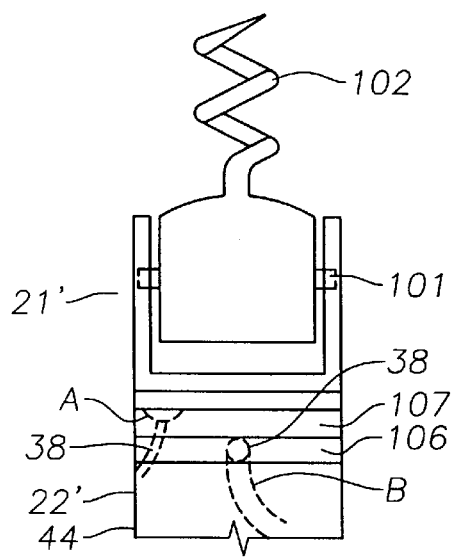
FIG. 18 is a side view of an alternative embodiment of the fixation mechanism of FIG. 17 showing an alternative conductor coil attachment.

Alternatively, as shown in FIG. 18, the conductor coil 38 may be coupled either to the proximal end of the housing 22' wherein the housing 22' and the hook 102 function as an electrode (position A shown in phantom), or to the inner surface of an annular electrode 106 that is insulated from the housing 22' by an insulator member 107 (see position B in phantom). Regardless of the particular connection point, the attachment may be via spot welding or other suitable attachment method.

Figure 19:
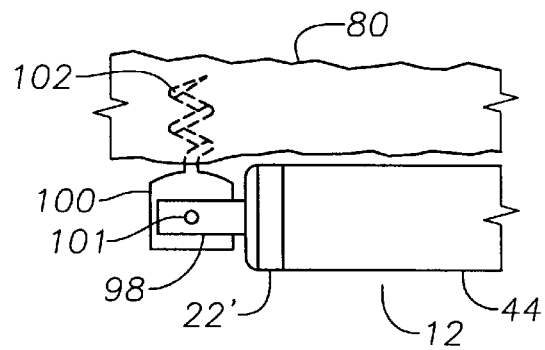
FIG. 19 is a side view of the fixation mechanism of FIG. 16 showing the lead pivoted into a position parallel to the epicardium.

In operation, the lead 12 may be placed proximate the epicardium 80 via the techniques described above. With the stylet 26 advanced into the bore 104 to longitudinally align the hook support 100 and the housing 22', the lead 12 is twisted to screw the hook 102 into the epicardium 80 as shown in FIG. 16. As shown in FIG. 19, the stylet 26 may be removed and the lead 12 pivoted to lay parallel to the surface of the epicardium 80 without introducing a bending moment into the lead 12. In this way, a screw-in lead tip may be employed via thoracoscopy with the lead 12 disposed parallel to the epicardium 80 without the bending moments associated with conventional lead designs.

Figure 20:
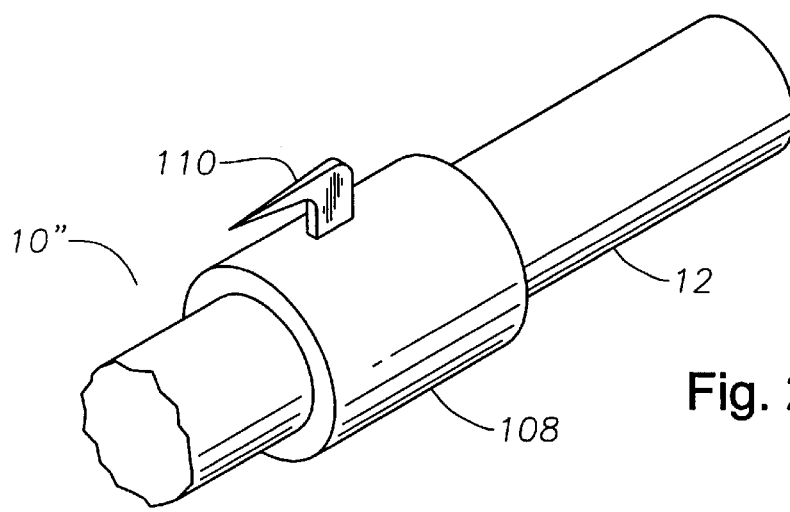
FIG. 20 is a pictorial view of the distal end of an alternate embodiment of the lead assembly incorporating a hook assembly that is slipped over the lead.

Heart surgeons may encounter situations where customization of the hook may be desirable. For example, preoperative imaging may not disclose unexpected surface conditions on the heart that become apparent during surgery. FIG. 20 discloses the distal end of an embodiment of a lead assembly 10" that may be customized as follows. The lead assembly 10" incorporates a tubular hook assembly 108 that may be slipped over the lead 12 and crimped into position at any longitudinal point along the lead 12. Care should be exercised in crimping the hook assembly 108 so that the underlying conductor wire (not shown) is not damaged. The hook assembly 108 includes a proximally projecting fixed hook 110. More than one such assembly 108 may be fixed to the lead 12. The hook assembly 108 may be fabricated in a variety of sizes with the hook 110 disposed in a variety of angles relative to the assembly 108. In this way, the surgeon may be provided with a kit of hook assemblies from which a particular assembly may be chosen to customize the lead 12 to a particular patient. The hook assembly 108 may be constructed from the same construction materials discussed above regarding the hook 24.

The foregoing description is centered around epicardial implantation using thoracoscopy. However, it should be understood that the lead assembly 10 may be employed endocardially using well known transvenous implantation techniques. As in the foregoing thoracoscopy procedure, manipulation of the lead assembly 10 during endocardial implantation will be accomplished by appropriate movements of the stylet 26 and the lead 12.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead comprising:
    a lead body having a proximal end and a distal end;
    a tubular housing coupled to said distal end of said lead and having a lumen;
    a hook having a first end pivotally coupled to said housing, a portion of said first end being disposed in said lumen, said hook having a first longitudinally projecting piercing member, said hook being pivotable between a first position wherein said first piercing member is disposed in spaced apart relation to said housing, and a second position wherein said first piercing member is disposed proximate to said housing;
    a biasing member coupled to said housing to bias said hook to said first position; and
    whereby said hook pivots to said second position in response to application of axial force to said portion of said first end to avoid piercing engagement with said heart tissue, and said hook pivots to said first position when force is removed so that said first piercing member of said hook may engage said heart tissue.

2. The active fixation mechanism of claim 1, wherein said biasing member comprises an elastomeric spring coupled to said housing.

3. The active fixation mechanism of claim 1, wherein said hook comprises an electrode for transmitting electrical signals carried by said lead.

4. The active fixation mechanism of claim 1, wherein said housing comprises an electrode for transmitting electronic signals carried by said lead.

5. The active fixation mechanism of claim 1, comprising a tine projecting from said housing for engaging a pericardial sac.

6. The active fixation mechanism of claim 1, wherein said hook comprises a second longitudinally projecting piercing member disposed in spaced apart relation to said housing for engaging said heart tissue, said second piercing member projecting in a direction opposite to said first piercing member.

7. A lead for fixation to heart tissue, comprising:
    an elongated elastic insulating tubular sheath;
    a tubular housing coupled to said sheath and having a lumen;
    a hook having a first end pivotally coupled to said housing and a first longitudinally projecting piercing member, a portion of said first end being disposed in said lumen, said hook being pivotable between a first position wherein said first piercing member is disposed in spaced apart relation to said housing, and a second position wherein said first piercing member is disposed proximate to said housing;
    a biasing member coupled to said housing to bias said hook to said first position; and
    whereby said hook pivots to said second position in response to application of axial force to said portion of said first end to avoid piercing engagement with said heart tissue, and said hook pivots to said first position when force is removed so that said first piercing member of said hook may engage said heart tissue.

8. The lead of claim 7, wherein said biasing member comprises an elastomeric spring coupled to said housing.

9. The lead of claim 7, wherein said hook comprises an electrode for transmitting electrical signals carried by said lead.

10. The lead of claim 7, wherein said housing comprises an electrode for transmitting electronic signals carried by said lead.

11. The lead of claim 7, comprising a tine projecting from said housing for engaging a pericardial sac.

12. The lead of claim 7, wherein said hook comprises a second longitudinally projecting piercing member disposed in spaced apart relation to said housing for engaging said heart tissue, said second piercing member projecting in a direction opposite to said first piercing member.

13. A lead assembly for fixation to heart tissue, comprising:
   an elongated tubular lead having a first distal end;
   a tubular housing coupled to said distal end and having a lumen;
   a hook having a first end coupled to said housing and a first longitudinally projecting piercing member being disposed in a spaced apart relation to said housing;
   a tubular introducer having a lumen for slidably receiving said lead, said introducer having a second distal end, an interior surface, and a guide slot in said interior surface to slidably receive said hook; and
   whereby said housing may be projected from said second distal end in a preselected angular orientation.

14. The lead assembly of claim 13, comprising:
   said hook having a first end pivotally coupled to said housing, a portion of said first end being disposed in said lumen, said hook being pivotable between a first position wherein said first piercing member is disposed in spaced apart relation to said housing, and a second position wherein said first piercing member is disposed proximate to said housing;
   a biasing member coupled to said housing to bias said hook to said first position; and
   whereby said hook pivots to said second position in response to application of axial force to said portion of said first end to avoid piercing engagement with said heart tissue, and said hook pivots to said first position when force is removed so that said first piercing member of said hook may engage said heart tissue.

15. The lead assembly of claim 13, comprising:
   said hook having a first end pivotally coupled to said housing, a portion of said first end being disposed in said lumen, said hook having a proximally disposed notch disposed in spaced apart relation to said housing, said hook being pivotable between a first position wherein said first piercing member is disposed in spaced apart relation to said housing, and a second position wherein said first piercing member is disposed proximate to said housing;
   a biasing member coupled to said housing to bias said hook to said second position;
   a tubular insert sleeve adapted to be slipped over said lead and engage said hook in said notch; and
   whereby said hook pivots to said first position in response to application of axial force by said insert sleeve on said hook, and said hook pivots to said second position when force is removed so that said first piercing member of said hook may engage said heart tissue.

16. The lead assembly of claim 14, wherein said biasing member comprises an elastomeric spring coupled to said housing.

17. The lead assembly of claim 13, wherein said hook comprises an electrode for transmitting electrical signals carried by said lead.

18. The lead assembly of claim 13, wherein said housing comprises an electrode for transmitting electronic signals carried by said lead.

19. The lead assembly of claim 13, comprising a tine projecting from said housing for engaging a pericardial sac.

20. The lead assembly of claim 13, wherein said hook comprises a second longitudinally projecting piercing member disposed in spaced apart relation to said housing for engaging said heart tissue, said second piercing member projecting in a direction opposite to said first piercing member.

21. A cardiac lead assembly comprising
   a lead lead body having a proximal end and a distal end;
   an active fixation mechanism for securing a cardiac lead to heart tissue coupled to said distal end of said lead body, said mechanism comprising:
   a tubular housing coupled to said lead;
   a support fork connected distally to said housing;
   a support pivotally coupled to said fork said support having a screw-in hook having a first end coupled to said support and a second end for piercing said heart tissue; and a bore opposite said hook for receiving a distal end of a stylet to prevent pivoting of said support
   whereby said support may be pivoted after said stylet is removed to permit said distal end of said lead body to lay generally parallel to said heart tissue after said screw-in hook is screwed into said tissue.

22. A lead assembly for fixation to heart tissue, comprising:
   an elongated tubular lead;
   a compressible tubular hook assembly housing slidably received on said lead and coupled thereto at a selected location when compressed;
   a hook assembly coupled to said housing, said hook assembly having a proximally projecting hook for engaging said heart tissue.

* * * * *

UNITED STATES PATENT AND TRADEMARK OFFICE
CERTIFICATE OF CORRECTION

PATENT NO.:5,871,532

DATED: Feb. 16, 1999

INVENTOR(S) :Schroeppel

It is certified that error appears in the above-identified patent and that said Letters Patent is hereby corrected as shown below:

In column 12, line 29, delete the first occurrence of "lead', therefor.

In column 12, lin 34, insert a comma after "said fork", therefor.

Signed and Sealed this

Sixth Day of June, 2000

*Attest:*

Q. TODD DICKINSON

*Attesting Officer*  *Director of Patents and Trademarks*